United States Patent
Sieroń

(10) Patent No.: US 11,583,690 B2
(45) Date of Patent: Feb. 21, 2023

(54) THERAPEUTIC DEVICE

(71) Applicant: Krzysztof Smela, Rzeszow (PL)

(72) Inventor: Aleksander Romuald Sieroń, Katowice (PL)

(73) Assignee: Krzysztof Smela, Rzeszow (PL)

( * ) Notice: Subject to any disclaimer, the term of this patent is extended or adjusted under 35 U.S.C. 154(b) by 30 days.

(21) Appl. No.: 16/473,132

(22) PCT Filed: Dec. 20, 2017

(86) PCT No.: PCT/PL2017/000129
§ 371 (c)(1),
(2) Date: Jun. 24, 2019

(87) PCT Pub. No.: WO2018/117880
PCT Pub. Date: Jun. 28, 2018

(65) Prior Publication Data
US 2019/0351247 A1    Nov. 21, 2019

(30) Foreign Application Priority Data

Dec. 23, 2016 (PL) .......................... 419964

(51) Int. Cl.
| | | |
|---|---|---|
| *A61N 2/00* | (2006.01) | |
| *A61G 10/02* | (2006.01) | |
| *A61H 33/14* | (2006.01) | |
| *A61N 2/02* | (2006.01) | |

(Continued)

(52) U.S. Cl.
CPC .......... *A61N 2/002* (2013.01); *A61G 10/026* (2013.01); *A61H 33/14* (2013.01); *A61N 2/02* (2013.01); *A61N 5/0616* (2013.01); *A61H 2033/141* (2013.01); *A61H 2201/10* (2013.01); *A61N 5/067* (2021.08); *A61N 2005/0652* (2013.01);

(Continued)

(58) Field of Classification Search
CPC .......... A61G 10/26; A61N 2/00; A61N 2/002; A61N 2/004; A61N 2/02
See application file for complete search history.

(56) References Cited

U.S. PATENT DOCUMENTS 5,935,516 A * 8/1999 Baugh ................. C12M 21/02
422/1
6,016,803 A * 1/2000 Volberg ............... A61G 10/026
128/202.12

(Continued)

FOREIGN PATENT DOCUMENTS

| | | |
|---|---|---|
| EP | 2838117 A1 | 2/2015 |
| EP | 3102011 A1 | 12/2016 |

(Continued)

OTHER PUBLICATIONS

International Search Report issued by the European Patent Office for International Patent Application No. PCT/PL2017/000129, dated May 30, 2018.

*Primary Examiner* — Carrie R Dorna
(74) *Attorney, Agent, or Firm* — Myers Wolin, LLC

(57) ABSTRACT

The subject matter of the invention is a therapeutic device in the form of a cylindrical chamber which comprises a hyperbaric chamber, LED matrices (5) and inductive coil rings (10, 11, 12, 13), constructed in one inseparable set in the form of a chamber of 200-280 cm in length and diameter of the round cylinder (70-130 cm).

7 Claims, 5 Drawing Sheets

(51) Int. Cl.
 A61N 5/06 (2006.01)
 A61N 5/067 (2006.01)
(52) U.S. Cl.
 CPC ............ *A61N 2005/0659* (2013.01); *A61N 2005/0661* (2013.01)

(56) References Cited

U.S. PATENT DOCUMENTS

| | | | |
|---|---|---|---|
| 2004/0193234 A1* | 9/2004 | Butler | A61N 5/0616 607/88 |
| 2004/0261796 A1 | 12/2004 | Butler | |
| 2010/0228183 A1* | 9/2010 | Sunnen | A61B 5/445 604/25 |

FOREIGN PATENT DOCUMENTS

| | | |
|---|---|---|
| FR | 2660548 A1 | 10/1991 |
| WO | 2008/146250 A2 | 12/2008 |

* cited by examiner

A B

THERAPEUTIC DEVICE

The subject matter of the invention is a therapeutic device, beneficial to use in combination therapy, i.e. hyperbaric oxygen therapy, hyperbaric ozone therapy, magnetotherapy, and low-emission laser therapy.

Hyperbaric therapy has been used in many fields of medicine, being in some disease entities the basic form of therapy, in others an alternative or supportive therapy. The safety of hyperbaric therapy has been proven in all age groups, including newborns and pregnant women. The essence of hyperbaric oxygen therapy is to increase the supply of oxygen to the damaged area, improve blood supply in the area damaged by narrowing the central vessels and increasing blood flow through the damaged tissues. Indications for the use of hyperbaric therapy can be divided into the following:

- it is recommended for, among others: necrotizing soft tissue infections, acute post-ischemic ischemia, grafts and skin lesions in danger of necrotizing, hard-healing wounds, chronic osteomyelitis, sudden deafness, decompression sickness, carbon monoxide poisoning
- it is optional for, among others: burns, toxic encephalopathy, anaerobic infections of lung and pleural space, reperfusion syndromes after vascular surgeries and limb replantation [Kościarz-Grzesiok et al. Acta Bio-Optica et Informatica Medica 3/2006, vol. 12].

Hyperbaric ozone therapy stimulates the immune system by increasing the release of defense factors, such as cytokines, interferons or interleukins. It supports the treatment of inflammatory conditions, burns, infected wounds, bed sores and ulcers. It is widely used in various types of infections, mainly fungal, and those caused by anaerobic bacteria, fighting them as well as preventing them from re-forming [Madej J. Alfa Medica Press 1998; 17-45]

Interest in the use of physiological methods in medicine results from the fact that new therapeutic methods which could support pharmacotherapy in many afflictions are being sought. The idea of stimulation is derived from the generally well known medical fact that properly dosed external stimuli cause the mobilization of immune and regenerative processes [Sieroń A. Europerespektywy. 2006; 3: 41].

Magnetic field is beneficial for tissue respiration and tissue regeneration, acting anti-inflammatory, anti-edema, relieving pain, increasing the absorption of oxygen by tissues. Laser therapy has analgesic effect, contributes to improvement of microcirculation and widening of blood vessels. Application of both of the methods simultaneously results in synergistic and even hyperadditional effects. Magnetic laser therapy is a non-invasive method with proven efficacy and safety of usage, it has been recognized by, among others, maintaining analgesic and anti-inflammatory effects, improving blood microcirculation, intensifying tissue oxidation, healing and regenerating wounds, accelerating the process of bone formation.

The following types of chambers are used in hyperbaric therapy:

- monoplace chambers, single-seated, intended for one patient, usually acrylic cylinders in shape, with steel covers on the sides. The patient is placed in the chamber in a lying position. The entire volume of the chamber is filled with oxygen. The patient can communicate with the medical staff via the intercom. There is no direct access to the patient during the treatment. There are no electrical devices installed inside the chamber due to the risk of fire. However, it is possible to install and receive radio signal and the transparent construction allows the patient to watch television programmes.
- multiplace chambers cylindrical or square in shape; able to accommodate up to a dozen or so people, enabling to enter and move freely inside. Each patient has their own oxygen intake place, administered by a mask or a special helmet. Patients are accompanied during the hyperbaric session by medical staff, supportive when needed. The main compartment of the chamber is filled with air. It is possible to install electrical devices inside the chamber, such as respirators, infusion pumps or monitoring systems. Such chambers also allow the medical staff to stay inside, which enables rapid medical intervention if needed, as well as conducting immediate medical treatment.
- portable—soft, folding chambers, most often used for personal therapy at a patient's home. Usually single-seated. The maximum operating pressure is 2.0 ATA—which is lower than in traditional, stationary hyperbaric chambers.
- local—small, portable chambers, for use only in the lower or upper extremities.

Currently, the main trend in the development of hyperbaric chambers is focusing on increasing patient's comfort during the sessions. Many manufacturers have also developed facilities for medical staff operating the chambers, e.g. assembling touch screens or computer programmes. During constructing this device, emphasis has been placed on the design. Proper design can increase the level of relaxation as well as the comfort of the patient, affecting the therapeutic effect of the treatment. Most of the chambers offered so far may arouse fear and cause unnecessary stress. It is also intended to make the device as lightweight as possible (e.g. polycarbonate fiber) to ensure certain mobility of the device.

Hitherto the chamber that would allow for full body impact and would have additional potential for therapy (including laser therapy and magnetotherapy) apart from hyperbaric therapy, has not been yet described. The only additional equipment usually located in multi-seat chambers includes: intravenous transfusion lines, electrical monitoring of a patient, including ECG, temperature and blood pressure, transcutaneous oxygen monitoring or apnea monitoring.

Additionally, in hyperbaric chambers during hyperbaric therapy, it is usually possible to use only one of the gases—oxygen or ozone and in order to use these therapies in succession, the patient would have to use two separate devices. The analogous situation is the case of other therapies—laser therapy and magnetotherapy. Each of the method has its own established indications in the medical world and the possibility of combining therapies together opens up quite new therapeutic possibilities. Usage of all these therapies in one device gives considerable comfort both to the patient as well as the staff operating the device. The patient is only prepared once for the session, there is no need to schedule or wait for further treatments. This may be the key aspect influencing the decision of people with certain degree of disability for whom mobility is a significant problem.

For the medical staff, it is also time saving as all the treatments in one place abolishes the need for preparation and subsequent disinfection after each treatment. Such a combined device will also save considerable space, which should be particularly appreciated by private individuals for whom renting a room is a significant cost. Previously used chambers have been usually stationary units installed in a given room permanently or portable chambers made of non-durable materials. Portable chambers often do not provide adequate air pressure. The device according to the invention combines the features of both types of the chambers—it ensures high tightness and durability to acquire the adequate pressure and the presence of portable gas generators enables potential transport. Mobility of the device is also a great advantage as it provides the possibility of efficient dislocation of the chamber. It also reduces the need for specialized technical support as well as installation time at a given facility.

The device according to the invention is designed so that by means of a special insulating apron, the patient's head can be excluded from the effect of oxygen and ozone under hyperbaric conditions, thus eliminating the necessity for using an oxygen mask during the therapy. The patient's head located beyond the effects of the treatment guarantees higher safety of the treatment and reduces the possibility of side effects such as complications related to pressure injury to the middle ear, paranasal sinuses and eyes. In addition, the usage of an insulating apron will enable intravenous injections and infusions into the patient's body during the session.

The device allows for 4 different therapies which can be complementary to one another. In addition, simultaneous usage of these therapies increases therapeutic efficacy in specific indications. Scientific research has shown that the effects of laser therapy and magnetotherapy demonstrate synergistic effects. Local application of low-energy laser therapy allows for increasing the effectiveness of oxygen therapy in selected areas of the body, resulting in increased performance as well as faster regeneration of the selected areas. This fact has been confirmed in scientific studies, hyperbaric laser therapy quickens healing wounds, including those with diabetic etiology and has a positive effect on the regeneration of Achilles' lesions.

Achieving synergistic effect of the combination therapy allows to reduce the number of treatments and quickens the patient's recovery.

The presented therapeutic system by means of the device according to the invention will also enable to eliminate pharmacotherapy as a supportive treatment. Antimicrobial and antifungal effects will be provided by ozone therapy in hyperbaric conditions, and analgesic as well as anti-inflammatory effects—magnetotherapy.

According to the results of our own research, the implementation of combination therapy will result in:
 increased effectiveness treatments of hard to heal wounds and diabetic foot versus hyperbaric oxygen therapy alone;
 reduction in wound size versus laser therapy alone, thereby increasing FGF-2 level (fibroblast growth factor) and VEGF (vascular endothelial growth factor);
 It can be an alternative to surgical procedures of Achilles tendon rupture, quickening its regeneration.

The purpose of the invention is to construct a device capable of treating many diseases. This device is based on several components which allow simultaneous or sequential therapy consisting of: hyperbaric oxygen and/or ozone therapy, variable magnetic therapy as well as low-emission laser therapy.

The device according to the invention is intended to remove the inconvenience associated with change of the device each time for a particular therapy, and at the same time, presentation of such a structure, which will be of small size and weight, will provide combination therapy in one and will simplify technological and medical service and support.

The essence of the invention is a therapeutic device in the form of a cylindrical chamber which contains a hyperbaric chamber, LED matrices and inductive coil rings, built into one inseparable set in the form of a chamber of 200-280 cm in length and a diameter of a circular cylinder of 70-130 cm.

A device with the hyperbaric chamber being an internal chamber of the device with an insulating apron.

Device with LED matrix located in the LED matrix frame, placed in the internal chamber of the device.

Device where the inductive coil rings are located in the coil slideways.

Device with coils in quantities ranging from 1 to 4.

Device with coils producing variable magnetic field with an induction of 100 microtesla to 5-10 millitesla, producing ion magnetic resonance.

Device with LED matrix and inductive coils of different geometric locations, depending on the need.

A device with an ozone generator located outside of the external chamber, a compressor.

EXAMPLE

A single chamber with dimensions of:
length: 200-280 cm
a diameter of a round cylinder forming a capsule: 70-130 cm.

The oxygen is supplied to the capsule by an oxygen generator located outside of the capsule and ozone is supplied from the ozone generator which is placed outside of the capsule.

Inside the capsule there are:
LED matrices which are responsible for low energy laser therapy (ledotherapy) and coils which enable obtaining variable magnetic field in the induction range from 100 microtesla to 5-10 militesla thanks to which ion magnetic resonance is acquired.

Both LED matrices and coils by their remote control location allow for different geometric locations depending on the needs of the patient.

The capsule design allows the head to be protected against the effect of oxygen and ozone by using a suitable medical collar.

For each type of action there are indicators enabling:
 estimation of oxygen concentration as well as oxygen partial pressure in the capsule,
 estimation of ozone concentration,
 estimation of the light radiation power in terms of infrared radiation (635 and 672 nm) and UVA,
 estimation of magnetic induction of the magnetic field as well as visualization of the course of the applied field.

The capsule has a hermetical lock with its own automatic time control protecting the patient from the possibility of prolonged influence and also with the possibility of emergency exit controlled by the patient including switching off all the devices.

Figure 1:
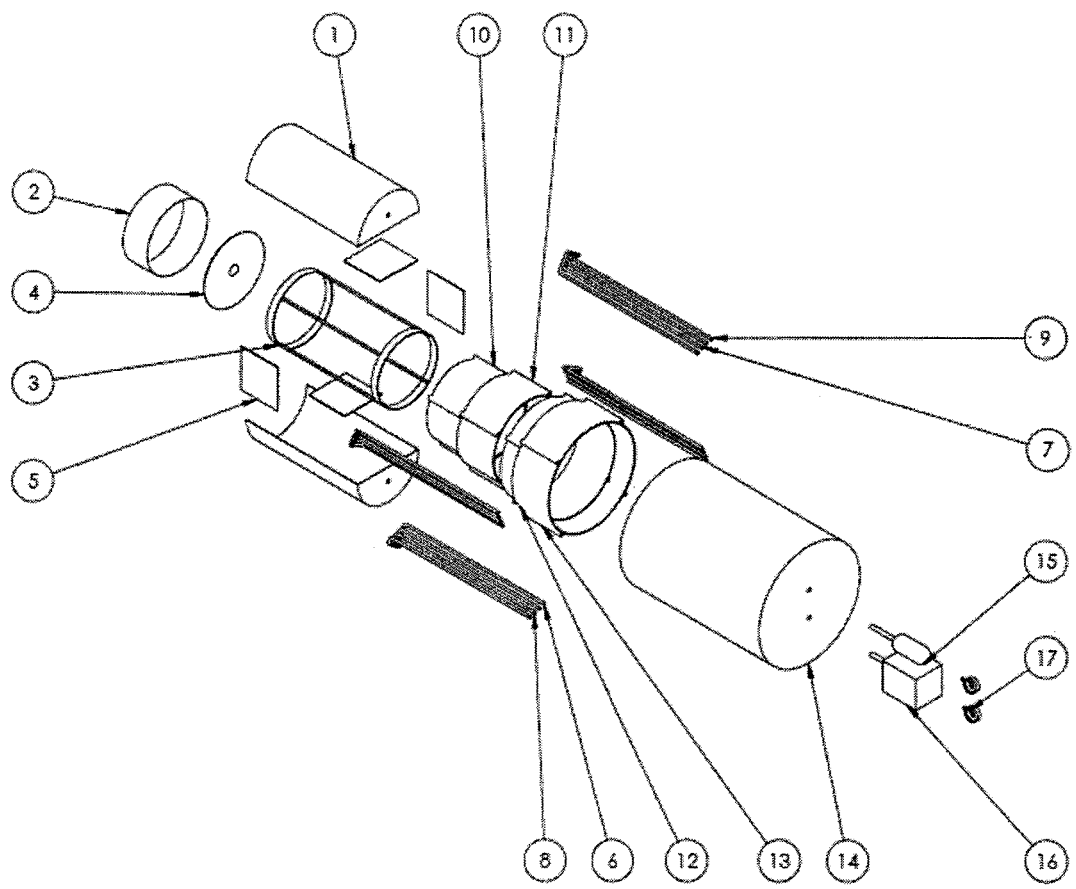
FIG. 1—depicts a hyperbaric chamber
FIG. 2—depicts a hyperbaric chamber in a section
FIG. 3—depicts a hyperbaric chamber—a frame
FIG. 4—depicts an arrangement of the inductive coils of the hyperbaric chamber
FIG. 5—depicts A) open internal chamber; B) closed internal chamber The invention illustrates the following example of non-limited construction

The wound regeneration device according to the invention is depicted in the figure, where FIG. 1 depicts the visualization of the hyperbaric chamber.

The device is in the form of a circular section of a cylinder with an internal chamber 1 and an internal chamber cover 2 as well as an insulating apron 4. An external chamber 14 which contains an ozone generator 15, a compressor 16 and a meter 17 is connected to the device. On the internal chamber 1, LED matrices frames 3 are mounted, where LED matrices 5 are placed. Apart from that, on the chamber 1 inductive coil rings 10, 11, 12, 13 are mounted, on which coil slideways 6, 7, 8, 9 are placed.

Figure 2:
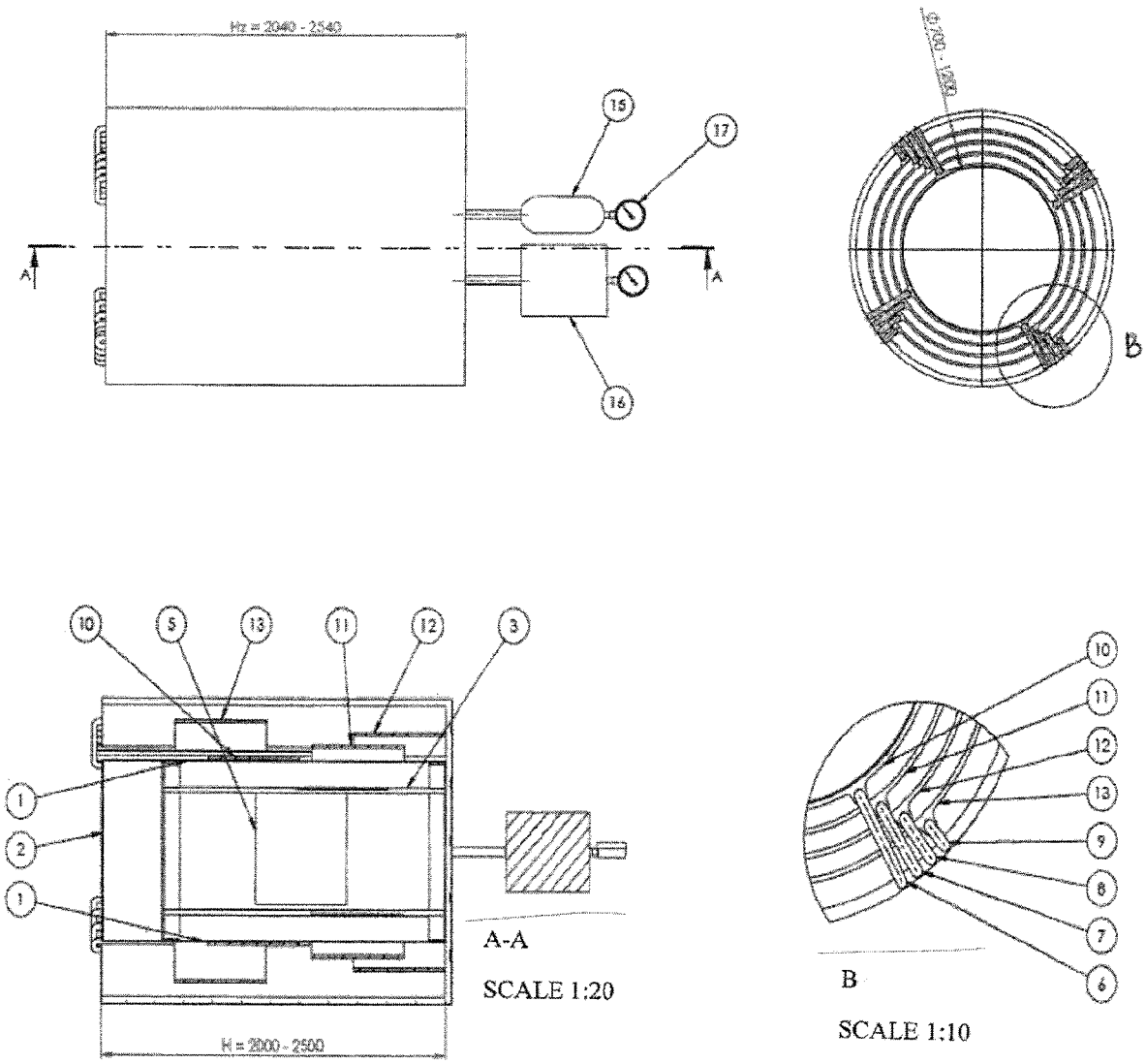

FIG. 2 depicts a cross-section of the hyperbaric chamber, with particular emphasis on the inductive coil rings (10, 11, 12, 13) and the coil slideways (6, 7, 8, 9).

Figure 3:
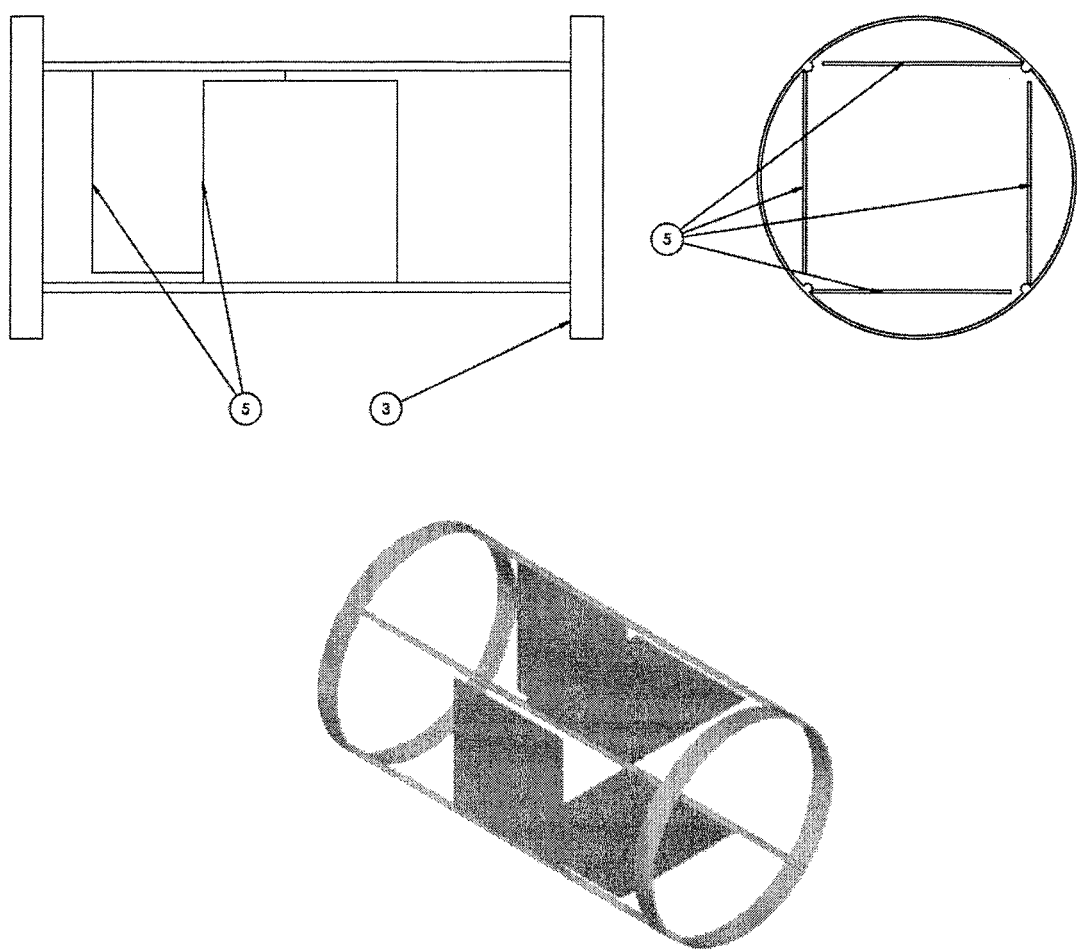

FIG. 3 depicts the layout of the LED matrix (5) in the frame (3) in the hyperbaric chamber.

Figure 4:
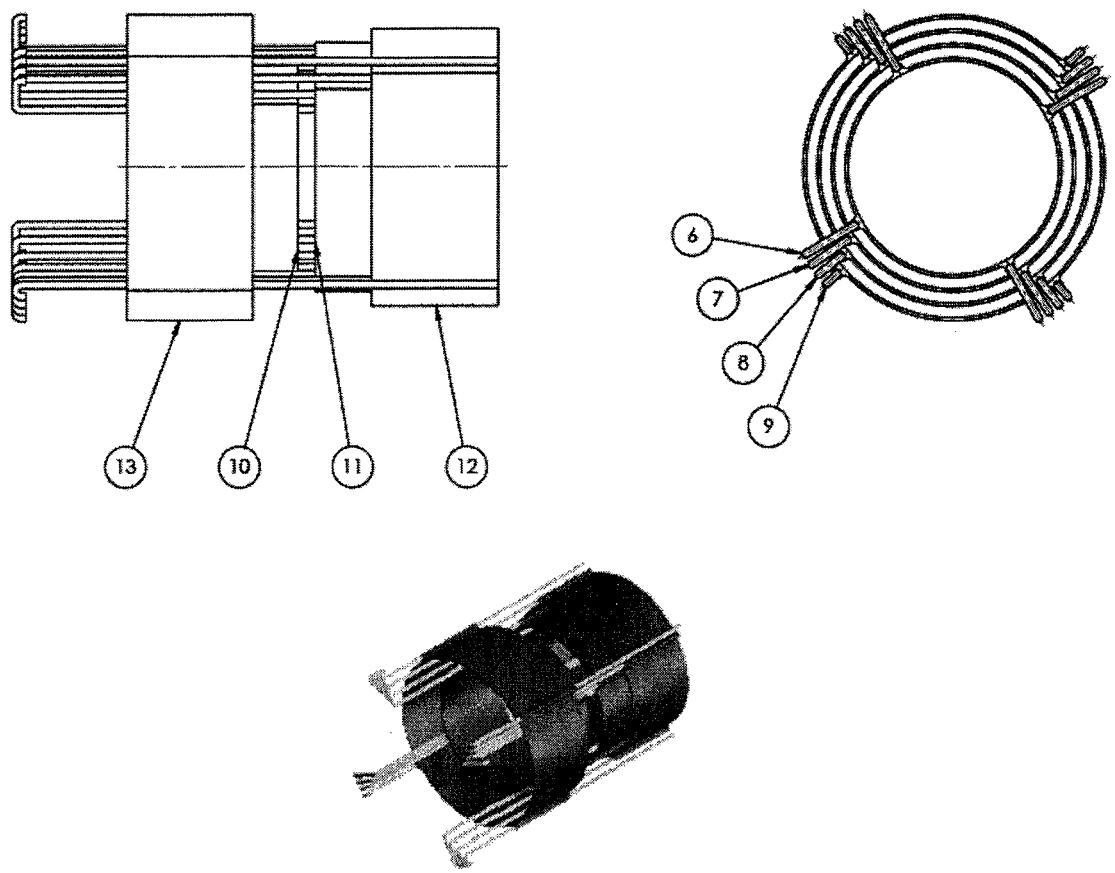

FIG. 4 depicts the layout of inductive coil rings (10, 11, 12, 13) in the coil slideways (6, 7, 8, 9).

Figure 5:
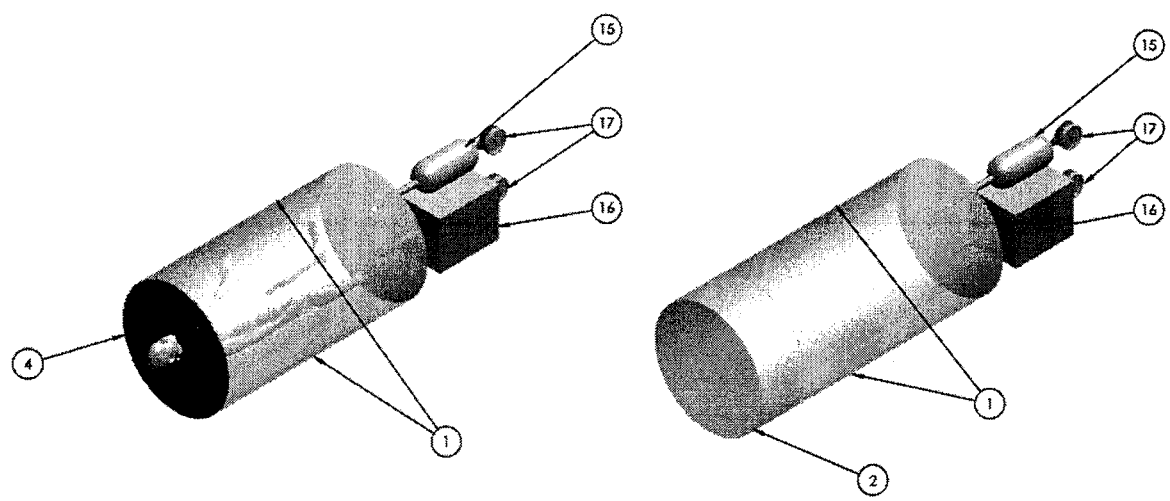

FIG. 5 depicts an open chamber visualization with a patient, an insulating apron (4) and a closed chamber with an internal cover (2). In addition, the device has a generator (15), a compressor (16), a meter (17).

| \multicolumn{4}{c}{The list of designations:} | | | |
|---|---|---|---|
| 17 | Meter | — | 2 |
| 16 | Compressor | — | 1 |
| 15 | Ozone generator | — | 1 |
| 14 | External chamber | — | 1 |
| 13 | Inductive coil ring | P4 | 1 |
| 12 | Inductive coil ring | P3 | 1 |
| 11 | Inductive coil ring | P2 | 1 |
| 10 | Inductive coil ring | P1 | 1 |
| 9 | Coil slideway | P4 | 4 |
| 8 | Coil slideway | P3 | 4 |
| 7 | Coil slideway | P2 | 4 |
| 6 | Coil slideway | P1 | 4 |
| 5 | LED matrix | — | 4 |
| 4 | Transparent insulation apron | — | 1 |
| 3 | LED matrices frame | — | 1 |
| 2 | Internal chamber cover | — | 1 |
| 1 | Internal chamber | — | 2 |
| Item | Name | Variant form | Pieces | Remarks |

The invention claimed is:

1. A therapeutic device in the form of a cylindrical chamber comprising a hyperbaric chamber configured to hold one or more pressurized gases, one or more LED matrices configured to generate light in the hyperbaric chamber, and one or more inductive coil rings arranged into one inseparable set in the form of a chamber of 200-280 cm in length and 70-130 cm in diameter, wherein
the one or more inductive coil rings are located in corresponding one or more coil slideways for adjusting the position of the one or more inductive coil rings.

2. The device according to claim 1, wherein the hyperbaric chamber is an internal chamber of the device with an insulating apron.

3. The device according to claim 1, wherein the one or more LED matrices are located in a LED matrix frame placed in the internal chamber of the device.

4. The device according to claim 1, wherein the device comprises 1 to 4 inductive coil rings.

5. The device according to claim 1, wherein the one or more LED matrices and the one or more inductive coil rings have remotely controlled locations and are configured to be rearrangeable to various geometric locations depending on the need.

6. The device according to claim 1, further comprising an ozone generator and a compressor placed outside the cylindrical chamber.

7. The device according to claim 1, wherein the one or more inductive coil rings produce a variable magnetic field with an induction of 100 microtesla to 10 millitesla, obtaining ion magnetic resonance.

* * * * *